United States Patent [19]

Meilland

[11] Plant 5,067

[45] Jul. 12, 1983

[54] ROSE PLANT — MEIMAGARMIC VARIETY

[75] Inventor: Marie L. Meilland, Antibes, France

[73] Assignee: Conard-Pyle Company, West Grove, Pa.

[21] Appl. No.: 324,255

[22] Filed: Nov. 23, 1981

[30] Foreign Application Priority Data

Dec. 29, 1980 [FR] France ..... 2980

[51] Int. Cl.[3] ..... A01H 5/00

[52] U.S. Cl. ..... Plt./11

[58] Field of Search ..... Plt./11

*Primary Examiner*—James R. Feyrer

*Attorney, Agent, or Firm*—Burns, Doane, Swecker & Mathis

[57] ABSTRACT

A new and distinct variety of Hybrid Tea rose plant is provided having highly attractive double flowers which are of empire yellow edged with an amaranth red flush. The new variety resulted from the crossing of the Meinuzeten and Mme. A. Meilland varieties, and is particularly suited for use in the beautification of parks and gardens.

1 Drawing Figure

SUMMARY OF THE INVENTION

The object of the present invention is to provide a new variety of rose plant of the Hybrid Tea Class which is distinguished from prior varieties by the following combination of characteristics:

from the physical standpoint the plant with light green adult wood has a semi-erect growth habit, forms dark green shiny leaves, and forms double flowers which are empire yellow and are edged with an amaranth red flush; and from the biological standpoint the plant has vigorous and regular vegetation, an abundant and repeated florescence, and the ability for its flowers to last a long time and for the petals to detach cleanly.

In view of these characteristics the new variety meets the needs of the horticultural industry and is particularly suited for ornamental use in parks and gardens.

The new variety resulted from artificial pollenation with the variety Meinuzeten (U.S. Plant Pat. No. 4,224) serving as the seed parent, and the variety Mme. A. Meilland (unpatented) serving as the pollen parent.

The seeds resulting from this pollenation were sown and 212 small plants were obtained which were physically and biologically different from each other. Selective study resulted in the identification of a single plant of the new variety. Extensive testing has confirmed the characteristics of the new variety.

The characteristics and properties of this new variety have been found to be transmissible by vegetative propagation, i.e. by grafting an eye.

The rose plant of the new variety has been named the Meimagarmic variety.

BRIEF DESCRIPTION OF THE PHOTOGRAPH

The accompanying photograph shows as nearly true as it is reasonably possible to make the same in a color illustration of this character, typical specimens of plant parts from three year old plants grafted on *Rosa froebelli* cultivated in the open air during September at Cannet des Maures, Var, France illustrated in:

FIG. 1 — a specimen of a young shoot;

FIG. 2 — a specimen of a bud before the sepals open;

FIG. 3 — a specimen of a bud at the opening of the sepals;

FIG. 4 — a specimen of a bud when the petals open;

FIG. 5 — a specimen of flower as opening begins;

FIG. 6 — a specimen of flower in the course of opening — plan view — obverse;

FIG. 7 — a specimen of a fully open flower — plan view — obverse;

FIG. 8 — a specimen of a fully open flower — plan view — reverse;

FIG. 9 — a specimen of a receptacle showing the arrangement of the pistils (sepals and stamens removed);

FIG. 10 — a specimen of a receptacle showing the arrangement of the stamens;

FIG. 11 — a specimen of the fruit;

FIG. 12 — a portion of a main branch showing the mature wood;

FIG. 13 — a portion of a young flowering stem;

FIG. 14 — a specimen of leaf with 3 leaflets — upper surface;

FIG. 15 — a specimen of leaf with 5 leaflets — under surface; and

FIG. 16 — a specimen of leaf with 7 leaflets — upper surface.

DETAILED DESCRIPTION

Figures 1, 2, 3, 4, 5, 6, 7, 8, 9, 10, 11, 12, 13, 14, 15, 16:
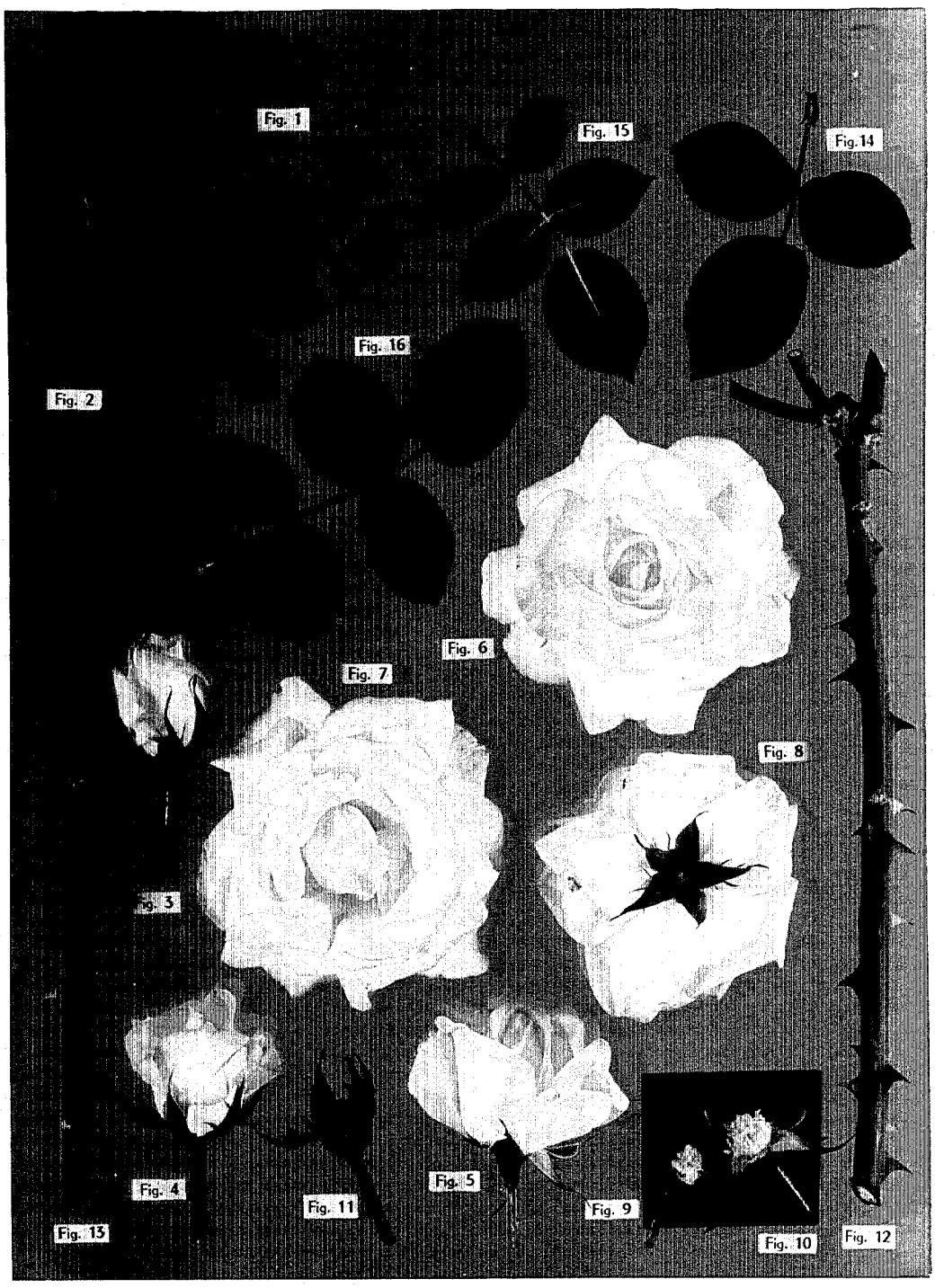

The plants described were grown outside during September at Cannet des Maures, Var, France.

The chart utilized in the identification of the colors is that of The Royal Horticultural Society (R.H.S. Colour Chart). The terminology preceding the numbered references to this chart has been added to designate in common terms the corresponding colors:

Class: Hybrid Tea.

Plant:

*Height.*—Approximately 0.7 to 0.85 m.

*Bearing.*—Semi-erect.

Branches:

*Color.*—Young stems: bronzed green — Yellow-Green Group 146A, widely shaded reddish. Mature wood: light green — Yellow-Green Group 146B.

*Thorns.*—Shape — upper edge: straight to slightly convex, slightly inflected towards the base. Shape — lower edge: concave. Size: fairly large. Quantity: medium. Color on young stems: reddish. Color on mature wood: straw, then light brown.

Foliage:

*Stipules.*—Adnate, pectinate, wide and linear.

*Petiole.*—Inner surface: grooved, reddish brown (young leaves), and medium green (adult leaves), more or less tomentose, with more or less glandular edges. Outer surface: light green, bears a few hooked prickles.

*Leaflets.*—Number: 3, 5 (the more often) and sometimes 7. Shape: oval, cordiform base and fairly wide summit. Teeth: simple and regular. Texture: very coriaceous. General effect: leaves fairly ample, dense and shiny.

*Color.*—Young leaves: upper surface: dark green — Yellow-Green Group 147A — darker. Under surface: medium green — Yellow-Green Group 148B.

Flowers:

*Number of flowers.*—Usually one flower per stem, sometimes pauciflorous (1 to 8 flowers per stem).

*Peduncle.*—Straight, rigid, more or less spotted reddish; it is fairly glandular and bears a few small hooked prickles. Length: approximately 4.5 to 5.5 cm.

*Sepals.*—Inner surface: tomentose, greenish; very rarely spotted reddish. Outer surface: light green, rarely spotted reddish; the outer sepals have glandular and slightly appendiculate edges.

*Bud.*—Shape: oblong. Length: 3.9 cm. on average, outside of the calyx, at opening of the sepals. Size: fairly large. Color on opening: upper and under surface: Naples Yellow — Yellow Group 11C — edged more or less with amaranth red — Red-Purple Group 63A.

*Flower.*—Shape: hollow cup shaped, petals slightly hemmed. Chorisis: double. Diameter: 14 cm. on average. Color — when first opening: inner surface and outer surface: empire yellow — Yellow Group 11D — edged with an amaranth red flush — Red-Purple Group 53B. Color — during the course of opening: inner surface: empire yellow — Yellow Group 11D — edged with an amaranth red flush — Red-Purple Group 63B. Outer surface: empire yellow — Yellow Group 11D — edged with a narrow and slight amaranth red flush — Red Purple Group 63B. Color when fully open: inner surface: whitish edged with a slight magenta pink flush — Red-Purple Group 64B. Outer surface: whitish with a narrow and slight magenta pink flush — Red-Purple Group 64B. Fragrance: light. Lasting quality: long. Corolla: petals: texture: firm. Shape: rounded. The claw is empire yellow — Yellow Group 11A inside, and Naples yellow — Yellow Group 11B outside; it becomes fully Naples yellow — Yellow Group 11B when fully open. Number: approximately 30 on average. The petals drop off cleanly. Stamens: number: approximately 70 on average. Anthers: ochre colored, normal. Pistils: number: 113 on average. Stigmas: normal, yellowish. Styles: whitish, with light fuchsine top, tomentose, more or less twisted, of unequal heights. Receptacle: light green; at the dehiscence of the anthers and is longitudinal section, it is narrow and funnel shaped.

Development:

*Vegetation.*—Vigorous and regular.

*Flowering.*—Abundant and repeated.

*Capacity for bearing fruit.*—Good.

*Resistance to frost.*—Spring: normal. Winter: normal.

*Resistance to diseases.*—Good.

I claim:

1. A new and distinct variety of Hybrid Tea rose plant, substantially as illustrated and described, by the fact that:

from the physical standpoint the plant with light green adult wood has a semi-erect growth habit, forms dark green shiny leaves, and forms double flowers which are empire yellow and are edged with an amaranth red flush; and from the biological standpoint the plant has vigorous and regular vegetation, an abundant and repeated florescence, the ability for its flowers to last a long time and for the petals to detach cleanly.

* * * * *